(12) United States Patent
Pae (10) Patent No.: US 10,004,430 B2
(45) Date of Patent: Jun. 26, 2018

(54) APPARATUS AND METHOD FOR DETECTING A FALL

(71) Applicant: LG CNS CO., LTD., Seoul (KR)

(72) Inventor: Jenny Pae, Seoul (KR)

(73) Assignee: LG CNS CO., LTD., Seoul (KR)

( * ) Notice: Subject to any disclaimer, the term of this patent is extended or adjusted under 35 U.S.C. 154(b) by 268 days.

(21) Appl. No.: 14/585,023

(22) Filed: Dec. 29, 2014

(65) Prior Publication Data

US 2016/0183847 A1     Jun. 30, 2016

(51) Int. Cl.
*A61B 5/11*      (2006.01)
*A61B 5/00*      (2006.01)

(52) U.S. Cl.
CPC .......... *A61B 5/1117* (2013.01); *A61B 5/1128* (2013.01); *A61B 5/6892* (2013.01); *A61B 5/002* (2013.01); *A61B 5/0013* (2013.01); *A61B 5/0022* (2013.01); *A61B 5/0077* (2013.01); *A61B 5/7282* (2013.01); *A61B 5/7285* (2013.01); *A61B 2562/0247* (2013.01)

(58) Field of Classification Search
CPC ... A61B 5/1117; A61B 5/0013; A61B 5/0077; A61B 5/1128; A61B 5/6892; A61B 5/7282; A61B 5/7285; A61B 2562/0247
See application file for complete search history.

(56) References Cited

U.S. PATENT DOCUMENTS

| | | | | |
|---|---|---|---|---|
| 6,515,586 | B1* | 2/2003 | Wymore | G08B 13/10 307/116 |
| 7,916,066 | B1* | 3/2011 | Osterweil | A61B 5/1117 340/573.1 |
| 2006/0049936 | A1* | 3/2006 | Collins, Jr. | A61B 5/1115 340/539.11 |
| 2007/0008156 | A1* | 1/2007 | Ueda | A47C 20/04 340/575 |
| 2007/0156031 | A1* | 7/2007 | Sullivan | A61B 5/6892 600/300 |
| 2007/0210917 | A1* | 9/2007 | Collins, Jr. | A61B 5/1117 340/539.1 |
| 2008/0213529 | A1* | 9/2008 | Gray | A47G 27/0475 428/44 |

(Continued)

FOREIGN PATENT DOCUMENTS

JP    H10-094525 A    4/1998
JP    2010-129078 A   6/2010
(Continued)

*Primary Examiner* — Patrick Edouard
*Assistant Examiner* — Eboni Hughes (57) ABSTRACT

A fall detection method performed by a fall detection server includes receiving electricity information from a piezoelectric plate disposed adjacent to a bed of a subject, performing a primary determination of whether or not the subject fell from the bed based on the electricity information, and triggering an imaging device to capture an image of a current state of the subject if it is determined that the subject fell, receiving video information including the image of the current state of the subject from the imaging device, and transmitting fall information relating to a fall of the subject to a terminal of the subject, the fall information including one or more of the primary determination result, trigger information of the imaging device, and the video information.

12 Claims, 8 Drawing Sheets

(56) References Cited

U.S. PATENT DOCUMENTS

| | | | |
|---|---|---|---|
| 2010/0286490 A1* | 11/2010 | Koverzin | G06F 19/3418 600/301 |
| 2012/0169467 A1* | 7/2012 | Condra | G06F 19/3418 340/8.1 |
| 2013/0127620 A1* | 5/2013 | Siebers | G08B 21/02 340/573.1 |
| 2014/0039351 A1* | 2/2014 | Mix | A61B 5/1114 600/587 |
| 2014/0267718 A1* | 9/2014 | Govro | G06Q 50/22 348/143 |
| 2015/0170494 A1* | 6/2015 | Hsu | G06F 19/3418 340/539.17 |
| 2016/0078750 A1* | 3/2016 | King | A61B 5/746 340/506 |
| 2016/0217664 A1* | 7/2016 | Bradford | E04F 15/02 |
| 2016/0228040 A1* | 8/2016 | Atarashi | A61B 5/747 |
| 2016/0235610 A1* | 8/2016 | Drake | A61G 7/018 |
| 2016/0284202 A1* | 9/2016 | Traughber | G08B 25/016 |
| 2016/0307429 A1* | 10/2016 | Hood | G08B 3/1016 |

FOREIGN PATENT DOCUMENTS

| | | |
|---|---|---|
| KR | 10-2012-0114893 A | 10/2012 |
| KR | 10-1438002 B1 | 9/2014 |

\* cited by examiner

APPARATUS AND METHOD FOR DETECTING A FALL

TECHNICAL FIELD

The present disclosure relates to an apparatus and method for detecting a fall.

BACKGROUND

As the result of a fall, an individual's bones or muscles may get hurt, after, for example, suddenly tripping over something or falling from something. In general, young children, who are inexperienced in moving their bodies, or elderly people, who have difficulties in moving their bodies, frequently experience fall accidents. In addition, other groups of people, such as medical patients, etc., may be susceptible to falls.

Furthermore, since falls occur as accidents, and regardless of intention, falls are highly likely to cause dangerous injuries. Thus, depending on a subject's state, a fall accident should be handled in a short time. In many cases, however, surrounding people may not recognize a state or position of a subject who has fallen. Thus, the opportunity for timely treating a person injured from a fall may be missed in many cases.

Recently, a fall detection method has been developed, which accurately recognizes the position of an individual that has experienced a fall and rapidly deals with the accident. Specifically, the fall detection method determines whether a person fell using a sensor mounted on the person, and accurately recognizes his/her position using GPS information of the sensor.

In this fall detection method, which uses a sensor, however, data should be wirelessly transmitted when a fall accident occurs. Thus, battery consumption or fall detection errors may increase, or filtering efficiency for error detection may be reduced. Furthermore, since this fall detection method detects a fall accident based on sensor information according to the motion of the person who has fallen, when the person provides sensor information, such as waving a hand, running, or colliding with something, the fall detection method may determine that a fall occurred based on the sensor information even when the above motion is not due to a fall accident.

Therefore, there is a demand for another fall detection method capable of reflecting other information as well as sensor information to determine whether a fall has occurred in order to accurately and rapidly detect a fall.

SUMMARY

Embodiments of the present disclosure are directed to a fall detection method capable of detecting whether or not a user fell using various pieces of information such as electricity information, video information, and/or audio information as well as sensor information.

Embodiments of the present disclosure are directed to a fall detection method capable of transmitting information on a state of a user to a terminal of a protector of the user when a fall of the user is detected.

A fall detection method performed by a fall detection server includes: receiving electricity information from a piezoelectric plate disposed adjacent to a bed of a subject; performing a primary determination of whether or not the subject fell from the bed based on the electricity information, and triggering an imaging device to capture an image of a current state of the subject if it is determined that the subject fell; receiving video information including the image of the current state of the subject from the imaging device; and transmitting fall information relating to a fall of the subject to a terminal of the subject, the fall information including one or more of the primary determination result, trigger information of the imaging device, and the video information.

The electricity information may be generated based on an electrical signal generated by a pressure applied to the piezoelectric plate by the subject.

The electricity information may be determined as the strength of a pressure applied to the piezoelectric plate by the subject.

The electricity information may be generated based on a contact area between a body of the subject and the piezoelectric plate as the body of the subject comes in contact with the piezoelectric plate.

The fall detection method may further include, after performing the primary determination of whether or not the subject fell: triggering a microphone to collect audio information which includes sound generated around the subject and a voice of the subject; and performing a secondary determination of whether or not the subject fell based on the audio information received from the triggered microphone.

Performing the secondary determination may include determining whether or not the voice of the subject included in the audio information substantially coincides with previously registered voice information of the subject that corresponds to a fall.

The fall information may further include position information of the subject having fallen from the bed, the secondary determination result, or both.

A fall detection method performed by a fall detection server includes: receiving, from a piezoelectric device, a first determination result obtained by determining whether or not a subject fell using electricity information generated based on at least one of a pressure applied to the piezoelectric device by the subject and a contact area between a body of the subject and the piezoelectric device; and transmitting fall information relating to a fall of the subject to a terminal of the subject, the fall information including the first determination result.

The fall detection method may further include: receiving, from an audio device, a second determination result obtained by determining whether or not the subject fell using audio information related to a fall of the subject, the audio device being triggered in response to a first control signal output from the piezoelectric device according to the first determination result and generating the audio information; and receiving, from an image device, video information including an image of a current state of the subject, the imaging device being triggered in response to a second control signal output from the audio device according to the second determination result, wherein the fall information includes one or more of the first determination result, the second determination result, trigger information of the imaging device, and the video information.

The fall detection method may further include: receiving, from an image device, video information including an image of a current state of the subject, the imaging device being triggered in response to a control signal output from the piezoelectric device according to the first determination result, wherein the fall information includes one or more of the first determination result, trigger information of the imaging device, and the video information.

A fall detection system includes: a fall detection server configured to receive electricity information from a piezoelectric plate arranged adjacent to a bed of a subject, perform a primary determination of whether or not the subject fell from the bed based on the electricity information, and generate a control signal if it is determined that the subject fell, receive video information including an image of a current state of the subject from an imaging device triggered in response to the control signal output from the fall detection server, and transmit fall information relating to a fall of the subject to a terminal of the subject, the fall information including one or more of the primary determination result, trigger information of the imaging device, and the video information.

The control signal may be a first control signal and the fall detection server may be configured to, after the primary determination: receive audio information related to the fall of the subject from a microphone triggered in response to the first control signal; perform a secondary determination of whether or not the subject fell based on the audio information, and generate a second control signal if it is determined that the subject fell as a result of the secondary determination, wherein the imaging device is triggered in response to one of the first control signal and the second control signal, and wherein the fall information includes one or more of the primary determination result, the second determination result, trigger information of the imaging device, and the video information.

The fall detection system may further include: a gateway configured to receive the electricity information from the piezoelectric plate, transmit the electricity information to the fall detection server, and receive the first control signal from the fall detection server, transmit the first control signal to the microphone, and receive the audio information from the microphone, transmit the audio information to the fall detection server and receive the second control signal from the fall detection server, transmit the second control signal to the imaging device, and receive the video information from the imaging device, and transmit the video information to the fall detection server.

The fall detection server may be configured to determine, in the primary determination, that the subject fell when the electricity information generated based on at least one of a pressure applied thereto by the subject and a contact area between a body of the subject and the piezoelectric plate is equal to or greater than a preset value, and determine, in the secondary determination, that the subject fell when a voice of the subject included in the audio information substantially coincides with previously registered voice information of the subject that corresponds to a fall.

A fall detection system includes: a piezoelectric device arranged adjacent to a bed of a subject and configured to determine whether or not the subject fell based on electricity information generated using at least one of a pressure applied thereto by the subject and a contact area between a body of the subject and the piezoelectric device; and a fall detection server configured to receive a determination result from the piezoelectric device and transmit fall information including the determination result to a terminal of the subject.

The fall detection system may further include: an audio device coupled to the piezoelectric device and configured to collect audio information which includes sound generated around the subject and a voice of the subject and determine whether or not the subject fell based on the audio information, wherein the piezoelectric device generates a first control signal if it is determined that the subject fell based on the electricity information, the audio device being triggered in response to the first control signal to collect the audio information, and wherein the fall detection server receives a determination result from the audio device and transmits the fall information including at least one of the determination result from the piezoelectric device and the determination result from the audio device to the terminal.

The fall detection system may further include: an imaging device coupled to at least one of the audio device and the piezoelectric device and configured to generate video information by capturing an image of a current state of the subject, wherein the audio device generates a second control signal for triggering the imaging device if it is determined that the subject fell based on the audio information, wherein the imaging device is triggered in response to one of the first control signal and the second control signal to capture the image of the current state of the subject, and wherein the fall detection server transmits the fall information including one or more of the determination result from the piezoelectric device, the determination result from the audio device, trigger information of the imaging device, and the video information to the terminal.

The fall detection system may further include: a gateway coupled to and disposed between the fall detection server and a group of the piezoelectric device, the audio device and the image device and configured to transmit the determination result from the piezoelectric device, the determination result from the audio device, and the video information to the fall detection server.

The piezoelectric device may determine that the subject fell when the electricity information is equal to or greater than a preset value.

The audio device may determine that the subject fell when the voice of the subject included in the audio information substantially coincides with previously registered voice information of the subject that corresponds to a fall.

According to embodiments of the present disclosure, a fall detection method may accurately recognize a current state of a user who got hurt from a fall by utilizing various pieces of information such as electricity information, video information, and audio information as well as sensor information.

Furthermore, the fall detection method may transmit information on a state of a user to a terminal of a protector of the user such that the protector rapidly treats the user who gets hurt from an unexpected fall.

DESCRIPTION OF EMBODIMENTS

Hereafter, embodiments of the present disclosure will be described below with reference to the accompanying drawings.

The following embodiments may be modified in various manners. Thus, the present disclosure should not be construed as limiting, but instead, embodiments should be construed to include all modifications, equivalents or substitutes thereof.

The terms used in the present disclosure are used for explaining specific embodiments, and do not limit embodiments. Terms in a singular form may include plural forms unless the contrary is indicated. In this specification, it should be understood that the meaning of "include/comprise" or "have" specifies a property, a figure, a step, a process, an element, a component, or a combination thereof which is described in the specification, without excluding one or more other properties, numbers, steps, processes, elements, components, or combinations thereof.

Terms used herein that are technical or scientific terms have the same meanings as the terms which are generally understood by those skilled in the art to which the present disclosure pertains, unless they are differently defined herein. Terms defined in a generally used dictionary may be interpreted to have meanings which coincide with contextual meanings in the related art. If terms are not clearly defined in this specification, they may not be interpreted as ideal or excessively formal or technical meanings.

In the accompanying drawings, like reference numerals refer to like elements, and duplicate descriptions thereof may be omitted. In the present disclosure, detailed descriptions related to well-known functions or configurations may be omitted so that the subject matter of the present disclosure is not unnecessarily obscured.

In the present disclosure, embodiments relate to methods, systems, and devices related to detecting when an individual or a subject has fallen. For convenience of description, the subject may be referred to as a "user." However, this term is not intended to be limiting. In some embodiments, a user's fall may be detected to facilitate treatment of the user.

Figure 1:
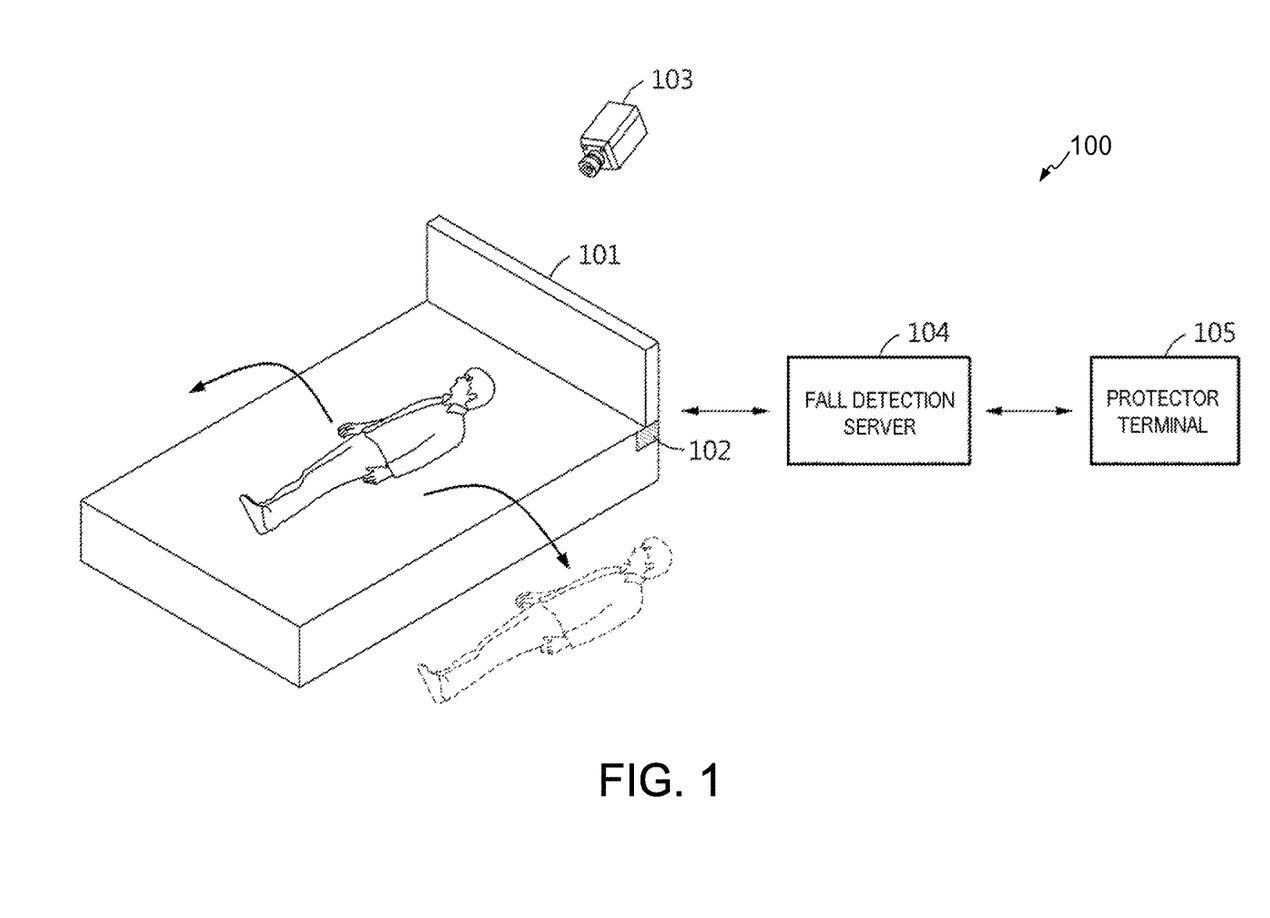
FIG. 1 illustrates a fall detection system according to an embodiment of the present disclosure.

FIG. 1 illustrates a fall detection system according to an embodiment of the present disclosure.

Referring to FIG. 1, a fall detection system 100 includes a fall detection device, a fall detection server 104, and a protector terminal 105 in order to check whether or not a user fell.

The fall detection device may detect a signal which is generated by a fall of a user, and include a piezoelectric plate (not shown) for sensing a pressure applied thereto by the user, an imaging device 103 for capturing an image of the surroundings of the user, and/or a microphone 102 for collecting sound generated around the user and/or a voice of the user.

The fall detection server 104 may receive one or more pieces of information related to the fall of the user from the fall detection device. The fall detection server 104 may determine whether or not the user fell based on various pieces of information such as electricity information generated by a pressure applied to the piezoelectric plate, video information obtained by the imaging device 103, and audio information obtained by the microphone 102. Thus, the fall detection server 104 may determine whether or not the user fell with more precision based on the various pieces of information.

Specifically, the fall detection server 104 may detect a pressure generated when the user on a bed 101 falls on a floor, through the use of a piezoelectric plate arranged adjacent to the bed 101. In an embodiment, the piezoelectric plate may be arranged around and/or on the bed 101 or on the floor, and detect a level of a pressure generated by a motion of the user. The fall detection server 104 can be carried or worn by the user, and implemented with any of various types of devices including a data communication device and a wearable device. Furthermore, the fall detection server 104 may be directly connected to the fall detection device.

The fall detection server 104 may receive electricity information related to whether or not electricity is generated through the pressure applied to the piezoelectric plate by the user, from the piezoelectric plate. The electricity information may include an electrical signal generated by the applied pressure. At this time, the fall detection server 104 may determine whether the electrical signal generated by the applied pressure has a magnitude equal to or greater than a preset magnitude. The electrical signal having a magnitude equal to or greater than the preset magnitude may be generated when a magnitude of the pressure applied to the piezoelectric plate by the user is equal to or greater than a predetermined magnitude. The electricity information may indicate a change of electricity generated by a pressure which is applied to the piezoelectric plate by an unexpected motion of the user. In other words, the magnitude of the electrical signal equal to or greater than the preset magnitude may indicate a magnitude of electricity generated by a fall of the user. The magnitude of the electrical signal may be determined based on the strength of the pressure applied to the piezoelectric plate and/or a contact area between a body of the user and the piezoelectric plate as the body of the user comes in contact with the piezoelectric plate.

The fall detection server 104 may primarily determine whether or not the user fell based on the electricity information. That is, the fall detection server 104 may primarily determine that the user fell if the electrical signal provided from the piezoelectric plate has an magnitude equal to or greater than the preset magnitude. Then, the fall detection server 104 may trigger the microphone 102 in response to the primary determination result. If it is triggered, the microphone 102 collects audio information, e.g., sound generated around the user and/or voice of the user.

The collected audio information is provided to the fall detection server 104. The fall detection server 104 may collect audio information generated by the fall of the user through the microphone 102 installed near a space where the electricity information was secured. In other words, the fall detection server 104 may additionally receive the audio information to perform additional verification for the fall of the user as an electrical signal having a magnitude that is expected due to the fall of the user is generated.

If the audio information is received, the fall detection server 104 may determine whether or not the audio information includes a user's voice related to the fall. At this time, the user's voice related to the fall may include various types of voices for notifying the fall of the user, and include a groan of pain which is let out from the user injured by the fall, a rescue request of the user, and/or a voice having an undefined pattern.

When the user's voice related to the fall is included in the audio information, i.e., a user's voice included in the audio information substantially coincides with previously registered voice information of the user that corresponds to the fall, the fall detection server 104 may trigger the imaging device 103. If it is triggered, the imaging device 103 captures an image of a current state of the user and generates video information including the image.

The fall detection server 104 may receive the video information on the current state of the user, which is provided by the imaging device 103, and transmit fall information related to the fall, which includes one or more of a determination result obtained based on the electricity information, a determination result obtained based on the audio information, and the video information to the protector terminal 105. In another embodiment, the fall detection server 104 may transmit trigger information indicating the triggering of the imaging device 103 to the protector terminal 105. The transmission of the trigger information is performed to notify the protector of the activation of the imaging device 103 such that the protector may check the current state of the user.

As described above, the fall detection server 104 may recognize the fall of the user by sequentially examining the pressure applied to the piezoelectric plate by the fall of the user and the sound generated around and/or by the user. Furthermore, the fall detection server 104 may finally transmit the video information on the current state of the user who fell and lies or sits on the floor, to the protector terminal 104. As a result, the protector may check the current state of the user using the video information, and take suitable actions for the treatment of the user.

The fall detection server 104 may check, stage by stage, whether a motion of the user is due to an unexpected fall or intentional motion based on electricity information, audio information, and video information, which are related to the motion of the user. Thus, the fall detection server 104 may provide a more effective operation of managing the fall of the user.

In another embodiment, the fall detection server 104 may trigger the imaging device 103 to check the current state of the user without performing an operation of recognizing a voice of the user. In this embodiment, the imaging device 103 may be triggered by a control signal that is generated by the fall detection server 104 based on the determination result obtained using the electricity information.

In still another embodiment, the fall detection server 104 may trigger an imaging device with a microphone in consideration of a situation in which the user cannot let out a voice when the user is unconscious from the fall.

The fall detection server 104 may transmit trigger information of the imaging device 103 or the video information on the current state of the user to the protector terminal 105. In another embodiment, the fall detection server 104 may transmit position information of the user having fallen from the bed 101 to the protector terminal 105.

In another embodiment, if the protector terminal 105 receives any of the determination result obtained based on the electricity information and the determination result obtained based on the audio information, the protector terminal 105 may send a command to the fall detection server 104 to trigger the imaging device 103. That is, embodiments are not limited to the above embodiments, and various changes and modifications thereof may be made.

Figure 2:
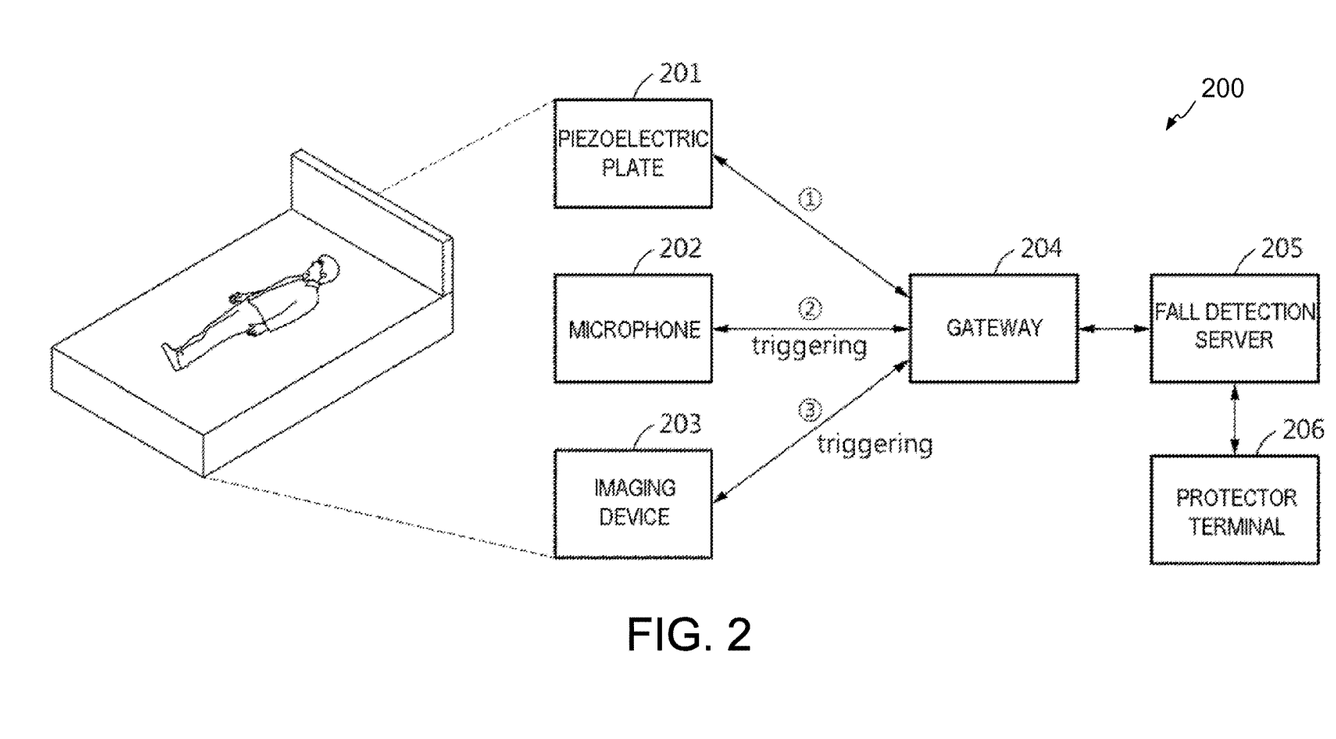
FIG. 2 illustrates a fall detection system using a gateway according to an embodiment of the present disclosure.

FIG. 2 illustrates an operation of a fall detection system using a gateway according to an embodiment of the present disclosure.

Referring to FIG. 2, a fall detection system 200 includes a fall detection device, a gateway 204, a fall detection server 205, and a protector terminal 206. The fall detection device includes a piezoelectric plate 201, a microphone 202, and an imaging device 203.

The gateway 204 may sequentially receive various pieces of information related to a fall of a user from the fall detection device according to steps (1) to (3). Specifically, the respective steps may be described as follows. The gateway 204 may receive the various pieces of information sensed by the piezoelectric plate 201, the microphone 202, and the imaging device 203 and transmit the various pieces of information to the fall detection server 205 as being interconnected with the fall detection server 205. The piezoelectric plate 201, the microphone 202, and the imaging device 203 may detect the fall of the user by sensing the various pieces of information.

Specifically, at step (1), the gateway 204 may receive electricity information, which is determined based on a pressure or contact area related to a motion or fall of the user and generated by the piezoelectric plate 201. After that, the gateway 204 may transmit the received electricity information to the fall detection server 205.

The fall detection server 205 may compare the electricity information received from the gateway 204 to a preset value which corresponds to a fall of the user. The fall detection server 205 may primarily determine whether or not the user fell based on the received electricity information. Then, when it is determined that the user fell, the fall detection server 205 may transmit a first control signal for triggering the microphone 202 to the gateway 204 in order to collect audio information related to the fall of the user.

The gateway 204 may receive the first control signal from the fall detection server 205, and transmit the first control signal to the microphone 202.

At step (2), the microphone 202 may be triggered in response to the first control signal received from the gateway 204. The gateway 204 may receive audio information, such as a voice of the user who got hurt from the fall, from the triggered microphone 202. Then, the gateway 204 may transmit the received audio information to the fall detection server 205. The fall detection server 205 may compare the audio information received from the gateway 204 to preset audio information such as a voice related to a fall of the user, and secondarily determine whether or not the user fell.

The fall detection server 205 may generated a second control signal for triggering the imaging device 203 according to the secondary determination result and transmit the second control signal to the gateway 204. The gateway 204 may receive the second control signal from the fall detection server 205, and transmit the received second control signal to the imaging device 203. In another embodiment, the fall detection server 205 may not generate the second control signal for triggering the imaging device 203 and, instead, may transmit to the protector terminal 206 the fall determination result obtained based on the electricity information from the piezoelectric plate 201 and/or the audio information from the microphone 202. In this embodiment, the protector terminal 206 may generate a control signal for triggering the imaging device 203, and the control signal is transmitted to the imaging device 203 via the fall detection server 205 and the gateway 204.

At step (3), the imaging device 203 may be triggered in response to the second control signal received from the gateway 204. The gateway 204 may collect video information including an image of the current state of the user from the imaging device 203. In an embodiment, the imaging device 203 may include an infrared camera. The gateway 204 may transmit the video information to the fall detection server 205.

The fall detection server 205 may receive the video information from the gateway 204, and finally determine whether or not the user fell. The fall detection server 205 may transmit the finally determined fall result and/or the video information to the protector terminal 206.

In short, the gateway 204 may receive various pieces of information related to a fall of a user from the piezoelectric plate 201, the microphone 202, and the imaging device 203. Then, the fall detection server 205 may determine, stage by stage, whether or not the fall of the user actually occurred based on the information received through the gateway 204.

In an embodiment, since the fall detection server 205 may receive the information related to the fall of the user through the gateway 204 paired with the fall detection device, the fall detection server 205 may accurately determine whether or not the user fell based on the respective pieces of information received from the gateway 204.

Figure 3:
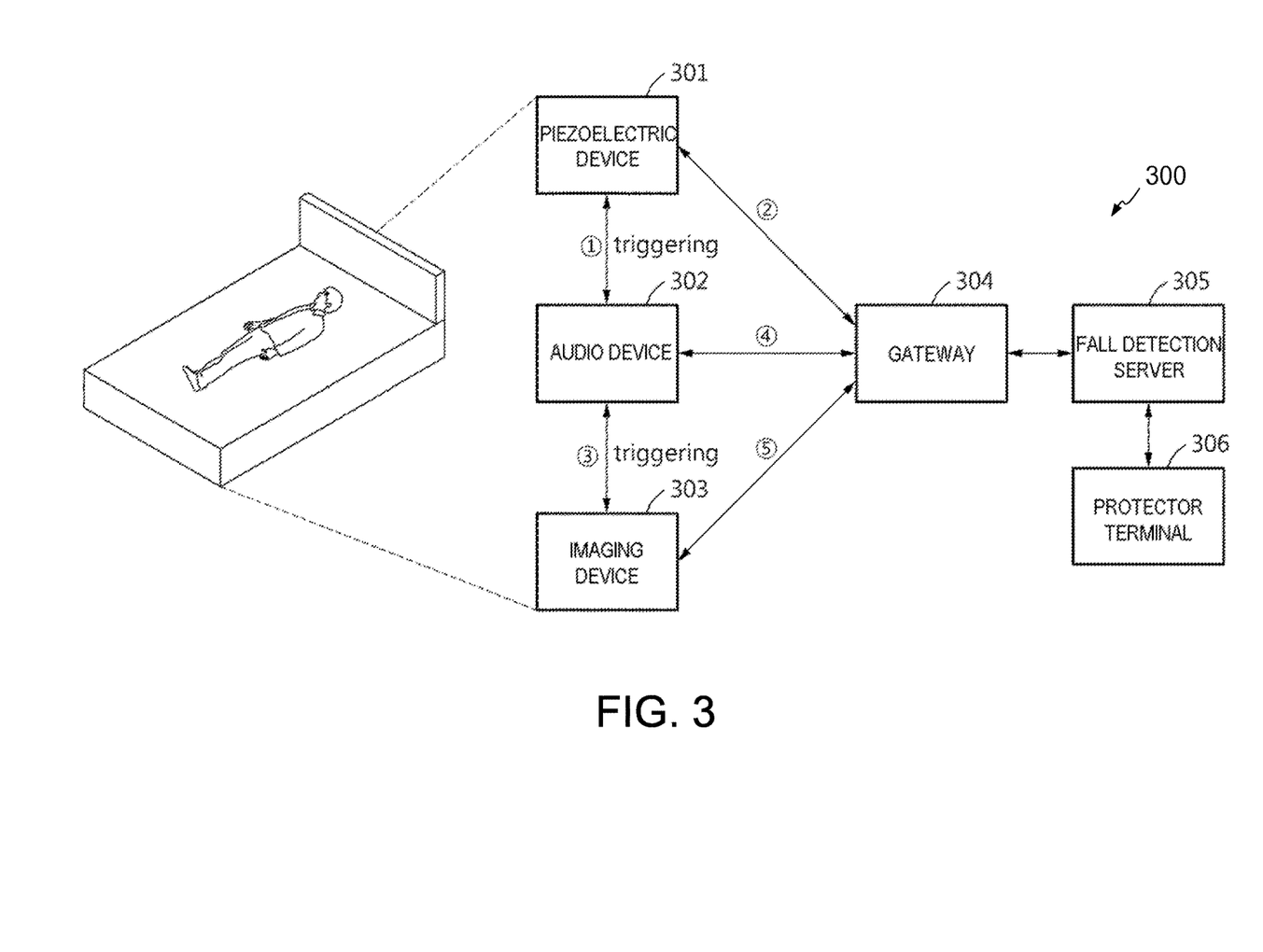
FIG. 3 illustrates a fall detection system using a gateway according to another embodiment of the present disclosure.

FIG. 3 illustrates a fall detection system using a gateway according to another embodiment of the present disclosure.

Referring to FIG. 3, a fall detection system 300 includes a fall detection device, a gateway 304, a fall detection server 305, and a protector terminal 306.

The fall detection device includes a piezoelectric device 301 including a piezoelectric plate, an audio device 302 including a microphone, and an imaging device 303, which collect information related to a fall of a user. The fall detection device may be sequentially triggered according to steps (1) to (5), but embodiments are not limited thereto. Hereinafter, the respective steps will be described in more detail.

The fall detection device may determine, by itself, whether or not the user fell based on signals related to the fall of the user, which are internally generated. The fall detection device may transmit a control signal for triggering another fall detection device according to the determination result on whether or not the user fell. Furthermore, the fall detection device may periodically update information on a standard for determining whether or not the user fell.

First of all, the piezoelectric device 301 may detect a pressure or contact area related to a fall due to a motion of the user, and generate an electrical signal corresponding to the detected pressure or contact area. Then, the piezoelectric device 301 may compare the electrical signal with a preset value, and determine whether or not the user fell based on the comparison result.

When it is determined that the user fell, at step (1) the piezoelectric device 301 may generate a first control signal for triggering the audio device 302 to collect audio information including a voice of the user that is related to the fall. The piezoelectric device 301 may transmit the first control signal to the audio device 302. The piezoelectric device 301 may also transmit the determination result, e.g., the transmission result of the first control signal for triggering the audio device 302, to the gateway 304 at step (2).

If the first control signal is received, the audio device 302 may be triggered in response to the first control signal received from the piezoelectric device 301, and powered on to collect ambient sound or voice of the user. The audio device 302 may compare the collected user voice or ambient sound with previously registered voice information of the user, and determine whether or not the user fell.

When it is determined that the user fell based on the audio information related to the fall of the user, the audio device 302 may transmit a second control signal for triggering the imaging device 303 to the imaging device 303 at step (3). At step (4), the audio device 302 may also transmit the determination result to the gateway 304. In an embodiment, the determination result may include a notification signal notifying that the second control signal for triggering the imaging device 303 was transmitted to the imaging device 303.

If the second control signal is received, the imaging device 303 may be triggered to collect video information including an image of a current state of the user in response to the second control signal transmitted from the audio device 302. The imaging device 303 may be triggered and powered on to collect the current image or surrounding image of the user who got hurt from the fall.

At step (5), the imaging device 303 may transmit the video information to the gateway 304. Then, the gateway 304 may transmit the received video information to the fall detection server 305. The fall detection server 305 may transmit the determination result related to the fall of the user to the protector terminal 306. Thus, the protector may be more rapidly called according to a determination result of the fall detection device due to a sudden emergency. Thus, the user may receive a prompt and proper treatment from the protector, e.g., a family, a caregiver, a doctor, a nurse or the like, according to the situation.

In the fall detection device, the piezoelectric device 301, the audio device 302, and the imaging device 303 may communicate with each other through a machine-to-machine (M2M) method to determine whether or not a user fell, and exchange information and/or signals relating to the fall of the user.

In this embodiment shown in FIG. 3, the fall detection server 305 receives various pieces of information through the gateway 304, but embodiments are not limited thereto. In another embodiment, the fall detection server 305 may directly receive various pieces of information and/or signals related to the fall of the user from the piezoelectric device 301, the audio device 302, and the imaging device 303. That is, the gateway 304 may be omitted.

Figure 4A:
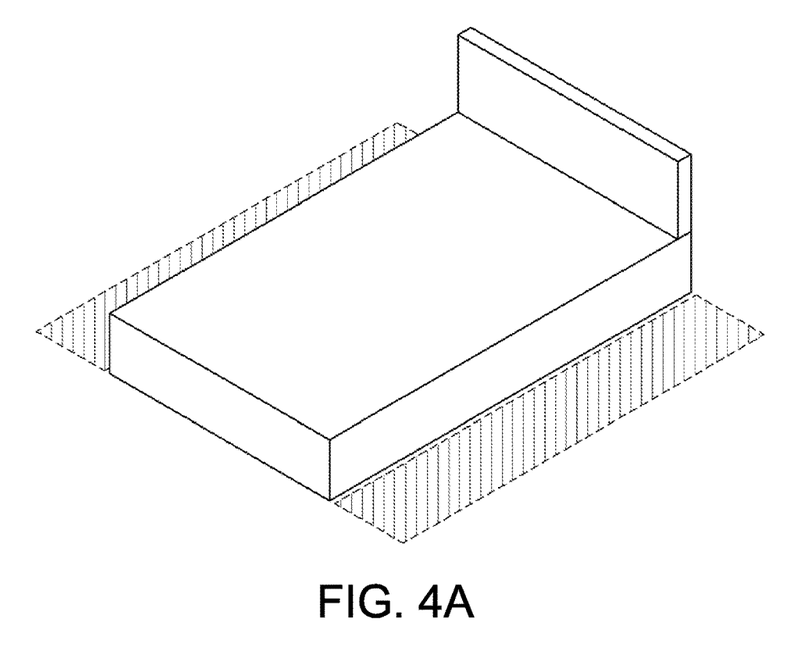
FIGS. 4A and 4B illustrate piezoelectric devices for detecting a pressure applied thereto by a fall of a user according to embodiments of the present disclosure.
Figure 4B:
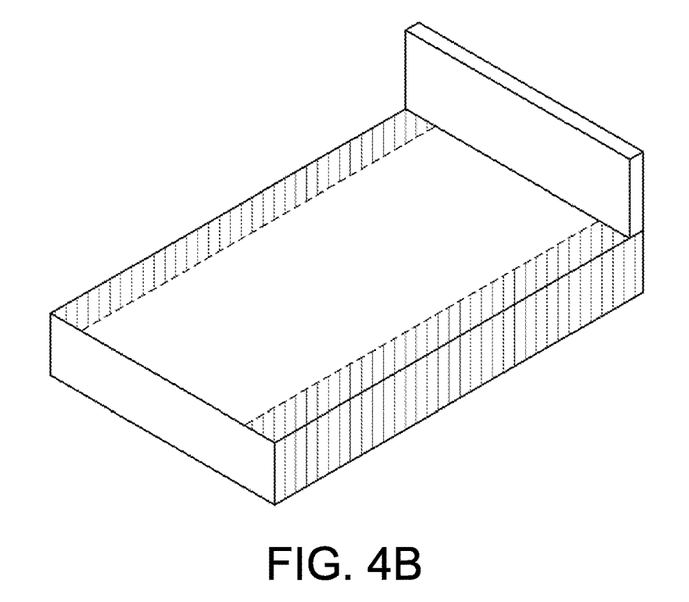

FIGS. 4A and 4B illustrate piezoelectric devices which detect a pressure applied thereto by a fall of a user according to an embodiment of the present disclosure.

Referring to FIG. 4A, the piezoelectric device includes a piezoelectric plate arranged adjacent to a bed so as to detect a pressure applied thereto by a motion of the user. Specifically, the piezoelectric plate may be arranged on a floor surface around the bed. In another embodiment, the piezoelectric plate may be arranged to be connected to the bottom surface of the bed. That is, the piezoelectric plate may be arranged on the bottom surface of the floor so as to detect a pressure applied thereto by a fall of the user in real time when the user falls from the bed.

Referring to FIG. 4B, the piezoelectric device includes a piezoelectric plate directly arranged on the bed. At this time, the piezoelectric plate may be arranged at edges of the bed in order to detect a pressure related to the fall of the user. That is, the piezoelectric plate may be arranged at portions with which the user comes in contact immediately before falling from the bed, and detect a pressure applied thereto by the fall in real time.

The piezoelectric device may generate electricity information used for primary determination for the fall of the user, and transmit the electricity information to a fall detection server. Furthermore, based on the electricity information, the fall detection server may determine whether or not the user fell by comparing the electricity information with a predetermined value. The fall detection server may trigger an audio device and/or an imaging device based on the determination result obtained based on the electricity information. Furthermore, as described above with reference to FIG. 3, the piezoelectric device may determine, by itself, whether or not the user fell, and trigger the audio device or the imaging device according to the determination result.

Figure 5A:
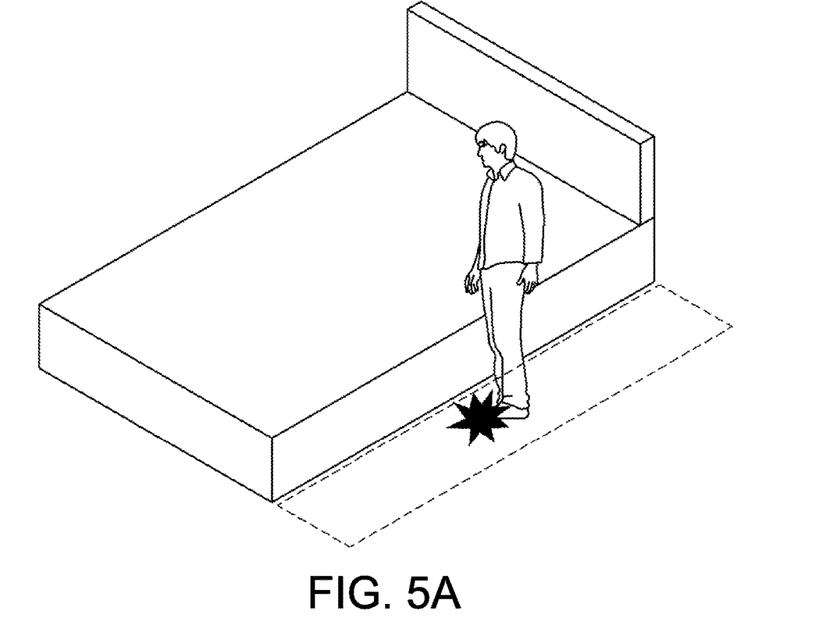
FIGS. 5A and 5B are views for explaining the strength of a pressure detected through a piezoelectric device according to embodiments of the present disclosure.
Figure 5B:
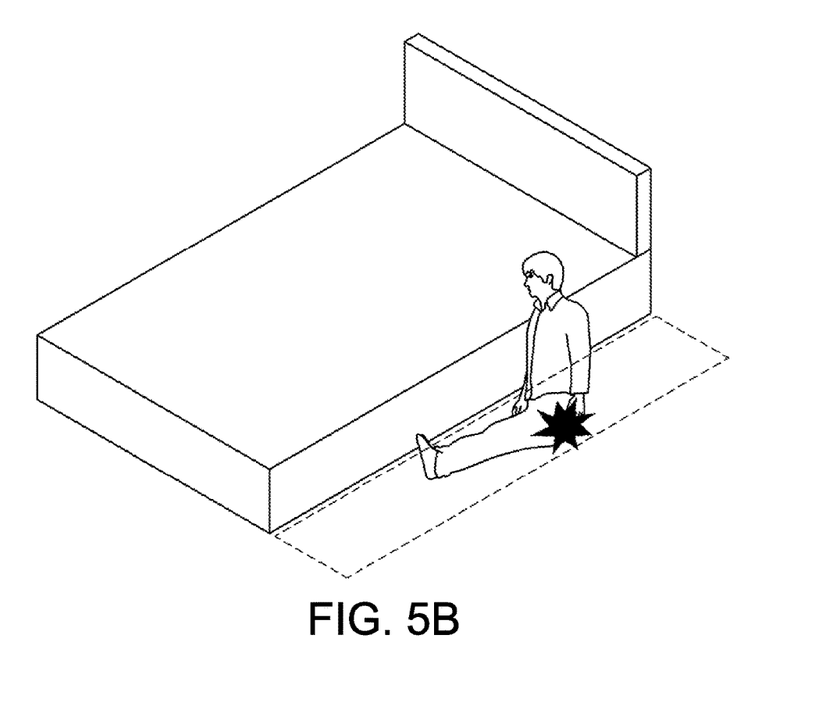

FIGS. 5A and 5B are diagrams for explaining the strength of a pressure detected through a piezoelectric device according to an embodiment of the present disclosure.

Referring to FIGS. 5A and 5B, a piezoelectric plate may detect a different strength depending on a pressure applied thereto by a user. The piezoelectric plate may generate electricity information in response to the detected strength of the pressure. Specifically, referring to FIG. 5A, the piezoelectric plate may detect the strength of a pressure applied thereto by a motion of the user. At this time, the user may apply a pressure, which may be generated in a daily life of the user, to the piezoelectric plate. The piezoelectric plate may generate an electrical signal from the pressure applied thereto by the user. Furthermore, a fall detection server may compare the electricity information corresponding to the electrical signal with a preset value, and determine whether the motion of the user is an intentional motion.

In other words, the fall detection server may determine that the motion of the user is an intentional motion when the electricity information is less than the preset value. At this time, the preset value may be differently set to each user based on physical information of a user, such as the weight and height of the user.

On the other hand, referring to FIG. 5B, the piezoelectric plate may detect a pressure applied thereto by a fall of the user, and generate an electrical signal from the applied pressure. At this time, the piezoelectric plate may detect a pressure which is generated during an accidental situation in which the user unintentionally trips or falls, unlike the pressure generated in FIG. 5A. In other words, the fall detection server may determine that the user fell when the electricity information generated by the fall of the user is equal to or greater than the preset value.

Thus, the fall detection server may determine whether or not the user fell from the bed based on the strength of the pressure applied to the piezoelectric plate by considering that a larger pressure is applied to the piezoelectric plate when the user accidentally falls compared to an intentional motion.

Figure 6A:
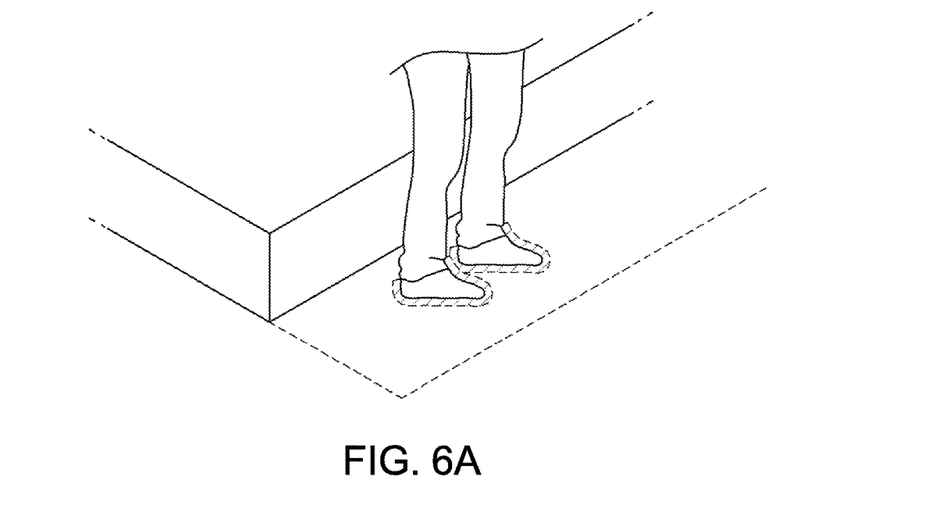
FIGS. 6A and 6B are views for explaining a contact area detected through a piezoelectric device according to embodiments of the present disclosure.
Figure 6B:
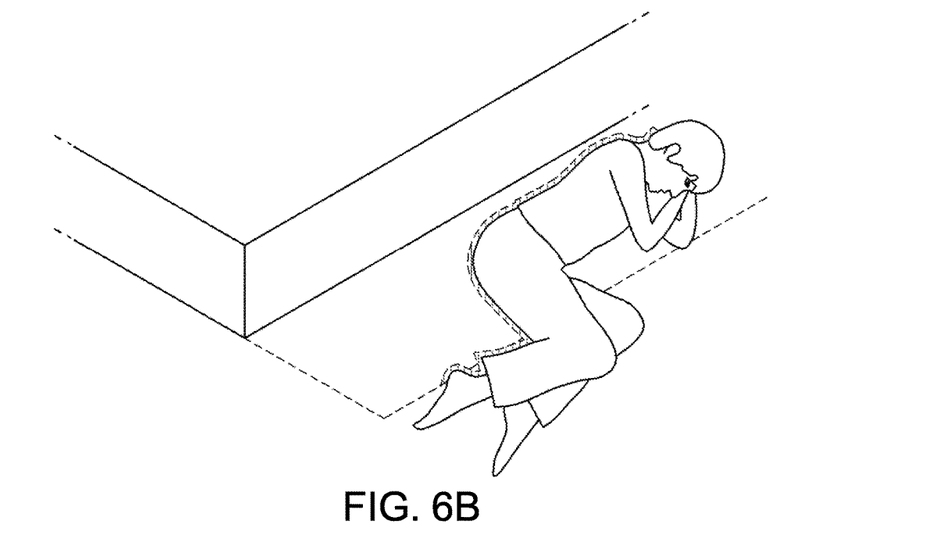

FIGS. 6A and 6B are diagrams for explaining a contact area detected through a piezoelectric device according to an embodiment of the present disclosure.

Referring to FIGS. 6A and 6B, a piezoelectric plate may detect an area of the piezoelectric plate with which a user comes in contact in order to determine whether or not the user fell. Specifically, referring to FIG. 6A, the piezoelectric plate may detect an area of the piezoelectric plate with which the user comes in contact. The user may take an action which is not related to a fall. For example, the user may walk or creep over the piezoelectric plate regardless of a fall. At this time, the area of the piezoelectric plate with which the user comes in contact may be smaller than an area of the piezoelectric plate with which the user comes in contact when the user fell. In such a case, a fall detection server may recognize that the action of the user is an intentional motion.

On the other hand, referring to FIG. 6B, the fall detection server may recognize that the user comes in contact with a large area of the bottom surface as the user fell. In other words, when the user fell from the bed, a heavy part of a body such as a back or breast first comes in contact with the bottom surface.

The fall detection server may recognize that the motion of the user is a fall of the user based on the area of the piezoelectric plate that is in contact with the body of the user.

Thus, the fall detection server may recognize the contact area of the piezoelectric plate based on a posture of the user when the user fell, thereby determining whether or not the user fell. In other words, the fall detection server may determine whether or not the user fell by considering that the user comes in contact with a larger area of the piezoelectric plate when the user fell compared to an intentional motion.

Figure 7A:
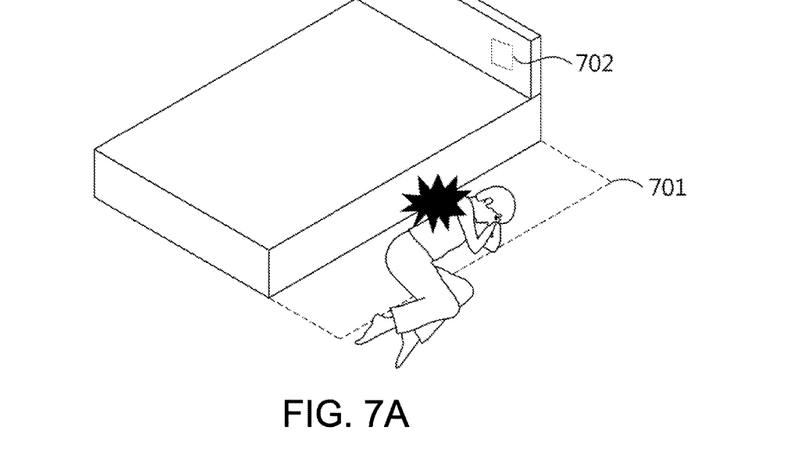
FIGS. 7A and 7B illustrate a piezoelectric device according to embodiments of the present disclosure.
Figure 7B:
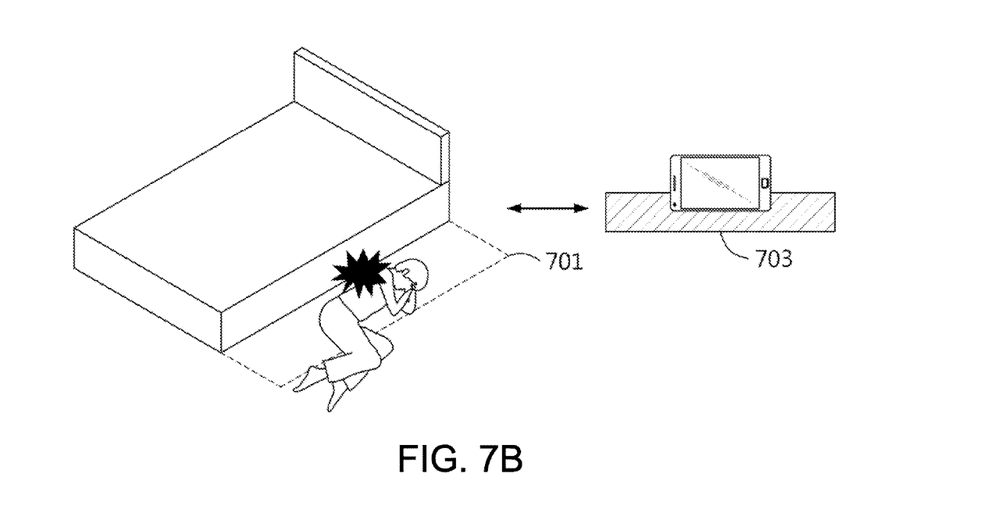

FIGS. 7A and 7B illustrate a piezoelectric device according to an embodiment of the present disclosure.

Referring to FIGS. 7A and 7B, a piezoelectric device 701 may transmit information on a situation in which a user fell to a protector terminal. At this time, the piezoelectric device 701 may determine whether or not the user fell, and transmit information on the situation of the user to the protector terminal through a calling device 702 wired thereto.

Referring to FIG. 7A, the piezoelectric plate 701 may be wired or wirelessly connected to the calling device 702 to call a doctor or nurse. The calling device 702 may be attached to a bed of the user. For example, the calling device 702 may be attached at various positions such as a frame of the bed and a wall beside the bed. The calling device 702 may include a nurse call which is formed in a button type and widely used in hospitals or sanatoriums.

In summary, the piezoelectric device 701 may be attached to the bed, and determine whether or not the user fell based on electricity information generated by the fall of the user. Furthermore, the piezoelectric device 701 may transmit the determination result to the protector terminal through the calling device 702 which is wired to the piezoelectric device 701.

Referring to FIG. 7B, the piezoelectric device 701 may be wired or wirelessly connected to a holder 703 of a user terminal. The piezoelectric device 701 may generate electricity information related to the fall of the user based on a pressure applied to the piezoelectric device 701 or a contact area of the piezoelectric device 701 with which the user comes in contact. The piezoelectric device 701 may determine whether or not the user fell based on the electricity information, and transmit the determination result to the holder 703 of the user terminal.

In this embodiment, since the holder 703 is connected to the user terminal, a separate microphone or imaging device may not be installed to collect information on the current situation of the user. As a result, it is possible to minimize installation of additional devices. Furthermore, when receiving a signal in a state where the holder 703 is in contact with the user terminal, the holder 703 may be connected to the protector terminal with an emergency call, e.g., a video call or voice call according to a data plan of the user terminal.

The piezoelectric device 701 may determine whether the pressure applied thereto through a user interface (UI) by the user is due to a fall, and transmit the determination result to the protector terminal through the calling device 702 or the holder 703. Therefore, the calling device 702 and the holder 703 may act as a gateway described in FIGS. 2 and 3.

Figure 8A:
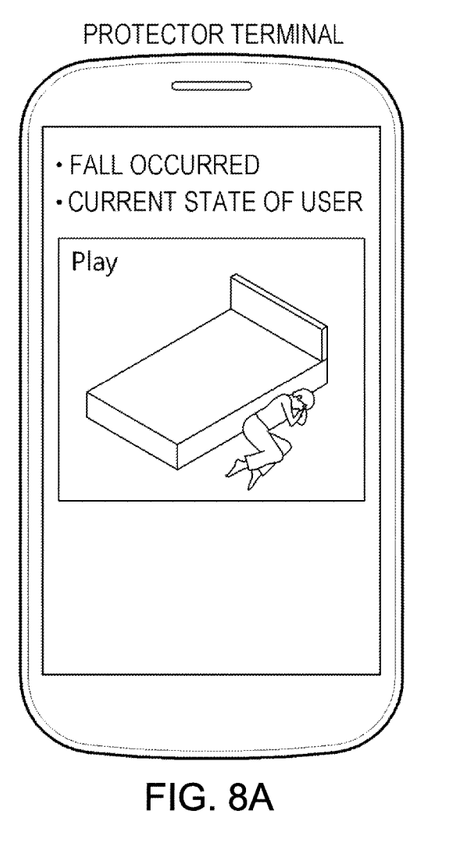
FIGS. 8A and 8B illustrate a state of a user who fell from a bed, which is displayed on a terminal of a protector according to embodiments of the present disclosure.
Figure 8B:
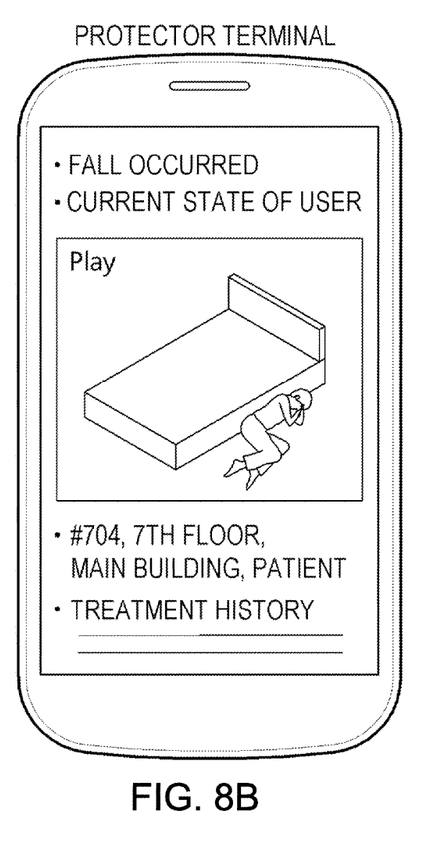

FIGS. 8A and 8B illustrate a state of a user who fell from a bed, which is displayed on a protector terminal according to an embodiment of the present disclosure.

Referring to FIGS. 8A and 8B, a fall detection server may transmit video information on the state of the user, which is secured by an imaging device when it is determined that the user fell, to the protector terminal. Furthermore, the fall detection server may further transmit position information of the user and a determination result of a piezoelectric device or an audio device to the protector terminal, in order to provide rapid treatment to the user who fell from the bed.

Referring to FIG. 8A, the protector terminal may include any of terminals of parents, brothers, sisters, caregivers and the like of the user. The protector terminal may receive the determination result and video information related to the fall of the user from the fall detection server, and display the received determination result and an image of the user such that the protector can check the determination result and the image of the user. For example, when a patient convalesces at home, a fall detection system may transmit a determination result and image related to a fall of the patient to a protector terminal. At this time, position information of the patient may be omitted since it is known where the patient is.

Referring to FIG. 8B, the protector terminal may include any of terminals of nurses and doctors who medically care the user. The protector terminal may receive the determination result and image related to the fall of the user from the fall detection server, and display the received determination result and image such that the protector can check the determination result and image. At this time, since the user is currently treated in a hospital or the like, the fall detection server may additionally transmit position information of the user to the protector terminal.

For example, when it is determined that the user fell, an imaging device may be triggered to capture an image of the user. Thus, the fall detection server may transmit the captured image and position information of the user to the protector terminal. Furthermore, the protector terminal may additionally display a treatment history in order to immediately provide proper treatment to the user who fell from the bed.

Furthermore, the protector terminal may control the imaging device to check a current state of the user in real time according to a current situation of the user. In other words, the protector terminal may enable the protector to operate the screen of the imaging device at an angle or direction desired by the protector. Thus, the protector may check the current state of the user with more precision. Furthermore, the protector terminal may control the screen direction of the imaging device to follow a voice of the user if it is determined that the user fell.

According to embodiments of the present disclosure, a fall detection server may sequentially verify a pressure applied by a user, a voice of the user, and a current image of the user in order to determine whether or not the user fell. Thus, the fall detection server may determine whether a motion of the user is due to a fall or intentional motion. Furthermore, the fall detection server may transmit information on a current state of the user to a protector terminal when it is determined that the motion of the user is due to a fall. Thus, a protector may provide the user with proper treatment based on information obtained through the protector terminal.

According to embodiments of the present disclosure, a fall detection method does not rely on only one piece of information, but may rely on various pieces of information to determine whether or not the user fell. The various pieces of information may include an impact of a body through which a fall of the user can be determined, a groan of the user, and the current position or motion of the user. Thus, the fall detection method may obtain a determination result for the fall of the user with more precision than a conventional method using only sensor information.

Furthermore, according to embodiments of the present disclosure, a fall detection method may detect a fall of a user in various places such as restrooms and stairs where a piezoelectric plate, a microphone, and an imaging device can be installed in addition to the above-described bed.

Methods according to embodiments of the present disclosure may be implemented in the form of program commands which can be executed through various computer units, and then written to computer readable media. The computer readable media may include a program command, a data file, a data structure, or a combination thereof. The program commands written to the media may be specially designed and configured for the present invention or include program commands publicly known to and used by those skilled in a computer software field.

While some embodiments have been described, it will be apparent to those skilled in the art that various changes and modifications may be made without departing from the spirit and scope of the present invention. For example, appropriate results can be achieved even when the above-described technologies are performed in a different order from those described and/or even when elements such as described systems, structures, apparatuses, and circuits are connected or combined in a different form from those described or are replaced or substituted by other elements or equivalents.

Thus, the scope of the present invention is not limited to the above-described embodiments, but may be defined by the following claims and equivalents to the claims.

What is claimed is:

1. A fall detection method performed by a fall detection server, the fall detection method comprising:
receiving electricity information from a piezoelectric plate through a gateway, the piezoelectric plate being disposed adjacent to a bed of a subject;
performing a primary determination of whether or not the subject fell from the bed based on the electricity information;
transmitting a first control signal to a microphone through the gateway if it is determined that the subject fell, thereby triggering the microphone to collect audio information which includes sound generated around the subject and a voice of the subject, the first control signal being generated according to a result of the primary determination;
receiving the audio information from the microphone through the gateway;
performing a secondary determination of whether or not the subject fell based on the audio information;
transmitting a second control signal to an imaging device through the gateway if it is determined that the subject fell, thereby triggering the imaging device to capture an image of a current state of the subject, the second control signal being generated according to a result of the secondary determination;
receiving video information from the imaging device through the gateway, the video information including the image of the current state of the subject; and
transmitting fall information relating to a fall of the subject to a protector terminal of the subject, the fall information including one or more of the primary determination result, the secondary determination result, trigger information of the imaging device, and the video information,
wherein the piezoelectric plate is arranged on a floor surface around the bed, and
wherein the gateway is coupled to and disposed between the fall detection server and the piezoelectric plate, between the fall detection server and the imaging device, and between the fall detection server and the microphone.

2. The fall detection method of claim 1, wherein the electricity information is generated based on an electrical signal generated by a pressure applied to the piezoelectric plate by the subject.

3. The fall detection method of claim 1, wherein the electricity information is determined as the strength of a pressure applied to the piezoelectric plate by the subject.

4. The fall detection method of claim 1, wherein the electricity information is generated based on a contact area between a body of the subject and the piezoelectric plate as the body of the subject comes in contact with the piezoelectric plate.

5. The fall detection method of claim 1, wherein performing the secondary determination comprises determining whether or not the voice of the subject included in the audio information substantially coincides with previously registered voice information of the subject that corresponds to a fall.

6. The fall detection method of claim 1, wherein the fall information further includes position information of the subject having fallen from the bed, the secondary determination result, or both.

7. A fall detection method performed by a fall detection server, the fall detection method comprising:
   receiving, from a piezoelectric device, a first determination result through a gateway, the first determination result being obtained by determining whether or not a subject fell from a bed using electricity information generated based on at least one of a pressure applied to the piezoelectric device by the subject and a contact area between a body of the subject and the piezoelectric device;
   receiving, from an audio device, a second determination result through the gateway, the second determination result being obtained by determining whether or not the subject fell from the bed using audio information which includes sound generated around the subject and a voice of the subject;
   receiving, from an imaging device, video information through the gateway, the video information including an image of a current state of the subject, the imaging device capturing the image of the current state of the subject; and
   transmitting fall information relating to a fall of the subject to a protector terminal of the subject, the fall information including one or more of the first determination result, the second determination result, trigger information of the imaging device, and the video information,
   wherein the piezoelectric device is arranged on a floor surface around the bed,
   wherein the gateway is coupled to and disposed between the fall detection server and the piezoelectric device, between the fall detection server and the imaging device, and between the fall detection server and the audio device,
   wherein the audio device is triggered in response to a first control signal output from the piezoelectric device according to the first determination result and generates the audio information, and
   wherein, when the audio device is triggered in response to the first control signal, the imaging device is triggered in response to a second control signal output from the audio device according to the second determination result.

8. A fall detection system comprising:
   a gateway; and
   a fall detection server configured to:
      receive electricity information from a piezoelectric plate through the gateway, the piezoelectric plate being arranged adjacent to a bed of a subject;
      perform a primary determination of whether or not the subject fell from the bed based on the electricity information, and generate a first control signal if it is determined that the subject fell as a result of the primary determination;
      transmit the first control signal to a microphone through the gateway, thereby triggering the microphone to collect audio information that is related to the fall of the subject;
      receive the audio information from the microphone through the gateway;
      perform a secondary determination of whether or not the subject fell based on the audio information, and generate a second control signal if it is determined that the subject fell as a result of the secondary determination;
      transmit the second control signal to an imaging device through the gateway, thereby triggering the imaging device to capture an image of a current state of the subject;
      receive video information from the imaging device through the gateway, the video information including the image of the current state of the subject; and
      transmit fall information relating to a fall of the subject to a protector terminal of the subject, the fall information including one or more of the primary determination result, the secondary determination result, trigger information of the imaging device, and the video information,
   wherein the piezoelectric plate is arranged on a floor surface around the bed, and
   wherein the gateway is coupled to and disposed between the fall detection server and the piezoelectric plate, between the fall detection server and the imaging device, and between the fall detection server and the microphone.

9. The fall detection system of claim 8, wherein the fall detection server is configured to:
   determine, in the primary determination, that the subject fell when the electricity information generated based on at least one of a pressure applied thereto by the subject and a contact area between a body of the subject and the piezoelectric plate is equal to or greater than a preset value; and
   determine, in the secondary determination, that the subject fell when a voice of the subject included in the audio information substantially coincides with previously registered voice information of the subject that corresponds to a fall.

10. A fall detection system comprising:
   a piezoelectric device arranged adjacent to a bed of a subject and configured to determine whether or not the subject fell from the bed based on electricity information generated using at least one of a pressure applied thereto by the subject and a contact area between a body of the subject and the piezoelectric device;
   an audio device coupled to the piezoelectric device, the audio device configured to collect audio information which includes sound generated around the subject and a voice of the subject and determine whether or not the subject fell based on the audio information;

a fall detection server configured to receive a first determination result from the piezoelectric device, receive a second determination result from the audio device, and transmit fall information to a protector terminal of the subject; and a gateway coupled to and disposed between the fall detection server and the piezoelectric device and between the fall detection server and the audio device, the gateway configured to transmit the first and second determination results to the fall detection server, wherein the fall information includes at least one of the first determination result and the second determination result, wherein the piezoelectric device is arranged on a floor surface around the bed, wherein the piezoelectric device generates a first control signal if it is determined that the subject fell based on the electricity information, the audio device being triggered in response to the first control signal to collect the audio information, wherein the system further comprises an imaging device coupled to at least one of the audio device and the piezoelectric device and configured to generate video information by capturing an image of a current state of the subject, wherein the audio device generates a second control signal for triggering the imaging device if it is determined that the subject fell based on the audio information, wherein the imaging device is triggered in response to one of the first control signal and the second control signal to capture the image of the current state of the subject, and wherein the gateway is further coupled to the imaging device, and the fall detection server receives the video information from the imaging device through the gateway, the fall detection server transmitting, to the protector terminal, the fall information including one or more of the first determination result from the piezoelectric device, the second determination result from the audio device, trigger information of the imaging device, and the video information.

11. The fall detection system of claim 10, wherein the piezoelectric device determines that the subject fell when the electricity information is equal to or greater than a preset value.

12. The fall detection system of claim 10, wherein the audio device determines that the subject fell when the voice of the subject included in the audio information substantially coincides with previously registered voice information of the subject that corresponds to a fall.

\* \* \* \* \*